(12) United States Patent
Singh et al.

(10) Patent No.: US 9,833,767 B2
(45) Date of Patent: Dec. 5, 2017

(54) SUPERABSORBENTS AND THE METHOD(S) OF OBTAINING THE SAME

(75) Inventors: Anupama Singh, New Delhi (IN); Druba Jyoti Sarkar, New Delhi (IN); Balraj Singh Parmar, New Delhi (IN)

(73) Assignee: Indian Council of Agricultural Research, New Delhi (IN)

( * ) Notice: Subject to any disclaimer, the term of this patent is extended or adjusted under 35 U.S.C. 154(b) by 660 days.

(21) Appl. No.: 13/701,342

(22) PCT Filed: Jun. 29, 2011

(86) PCT No.: PCT/IN2011/000432
§ 371 (c)(1),
(2), (4) Date: Nov. 30, 2012

(87) PCT Pub. No.: WO2012/001707
PCT Pub. Date: Jan. 5, 2012

(65) Prior Publication Data
US 2013/0069000 A1    Mar. 21, 2013

(30) Foreign Application Priority Data
Jul. 2, 2010 (IN) .......................... 1292/DEL/2010

(51) Int. Cl.
| | | |
|---|---|---|
| *B01J 20/26* | (2006.01) | |
| *A61L 15/60* | (2006.01) | |
| *C08F 251/00* | (2006.01) | |
| *C08F 292/00* | (2006.01) | |
| *C09K 17/40* | (2006.01) | |
| *B01J 20/30* | (2006.01) | |

(52) U.S. Cl.
CPC ............ *B01J 20/267* (2013.01); *A61L 15/60* (2013.01); *B01J 20/3028* (2013.01); *C08F 251/00* (2013.01); *C08F 292/00* (2013.01); *C09K 17/40* (2013.01)

(58) Field of Classification Search
None
See application file for complete search history.

(56) References Cited

U.S. PATENT DOCUMENTS

| | | |
|---|---|---|
| 3,229,769 A | 1/1966 | Bashaw et al. |
| 3,586,648 A | 6/1971 | Sambeth et al. |
| 3,669,103 A | 6/1972 | Harper et al. |
| 3,670,731 A | 6/1972 | Harmon |
| 4,102,340 A | 7/1978 | Mesek et al. |
| 4,244,880 A | 1/1981 | Alexander et al. |
| 4,559,074 A | 12/1985 | Clarke |
| 4,579,578 A | 4/1986 | Cooke |
| 5,059,654 A * | 10/1991 | Hou et al. .................... 525/54.1 |
| 5,064,653 A | 11/1991 | Sessions et al. |
| 5,145,906 A | 9/1992 | Chambers et al. |
| 5,629,360 A | 5/1997 | Askari et al. |
| 6,387,978 B2 | 5/2002 | Ronan et al. |
| 6,500,947 B1 | 12/2002 | West et al. |
| 2010/0198177 A1* | 8/2010 | Yahiaoui ................. A61F 13/82 604/359 |

FOREIGN PATENT DOCUMENTS

| | | |
|---|---|---|
| CN | 85102156 A | 1/1987 |
| CN | 1519034 A | 8/2004 |
| CN | 1544497 A | 11/2004 |
| CN | 101402708 A | 4/2009 |
| CN | 101712785 A | 5/2010 |
| IN | 250349 | 12/2011 |

OTHER PUBLICATIONS

Wu et al., "Modeling Young's modulus of rubber-clay nanocomposites using composite theories," Polymer Testing, 2004, pp. 903-909, vol. 23.

Singh, Vandana et al., "Microwave Promoted Synthesis of Chitosan-Graft-Poly(acrylonitrile)," Journal of Applied Polymer Science, 2005, pp. 820-825, vol. 95.

Chang, Jin-Hae et al., "Poly(lactic acid) nanocomposites: comparison of their properties with montmorillonite and synthetic mica (II)," Polymer, 2003, pp. 3715-3720, vol. 44.

(Continued)

*Primary Examiner* — Necholus Ogden, Jr.
(74) *Attorney, Agent, or Firm* — The Webb Law Firm (57) ABSTRACT

This invention relates to novel non-composite and composite superabsorbents, wherein the dry superabsorbents are xerogels, more particularly the bio-xerogels or the composites, particularly the biocomposites, more particularly the bionanocomposites and the method(s) of obtaining the same characterized by simultaneous in situ grafting and cross linking of ethylinically unsaturated monomers on to a single biopolymer of plant or animal origin, or on combination of different biopolymers or biopolymer(s) or/and clay(s), in a homogeneous polar phase, in the presence of initiator and crosslinker of chemical or non-chemical origin, at a temperature of 40 to 90° C., achieved by conventional or microwave heating, reaction time varying from instantaneous to 48 hours, involving use of alkali, either in situ or post reaction at room or elevated temperatures for achieving superior absorbency, in an inert or ambient reaction environment, to yield a neutral or near neutral product.

19 Claims, 1 Drawing Sheet

(56) References Cited

OTHER PUBLICATIONS

Gao, Deyu et al., "Structure and Mechanical Properties of Superabsorbent Poly(acrylamide)-Montmorillonite Composite Hydrogels," Polymer Gels and Networks, 1993, pp. 225-246, vol. 1, Issue 4.

Kvien, Ingvild et al., "Characterization of Cellulose Whiskers and Their Nanocomposites by Atomic Force and Electron Microscopy," Biomacromolecules, 2005, pp. 3160-3165, vol. 6.

Mathew, Aji P. et al., "Mechanical Properties of Biodegradable Composites from Poly Lactic Acid (PLA) and Microcrystalline Cellulose (MCC)," Journal of Applied Polymer Science, 2005, pp. 2014-2025, vol. 97.

Mathew, Aji P. et al.,"The Structure and Mechanical Properties of Cellulose Nanocomposites Prepared by Twin Screw Extrusion," Cellulose Nanocomposites, Jul. 13, 2006, pp. 114-131, Chapter 9, ACS Symposium Series, vol. 938, peer-reviewed book chapter.

McGlashan, Stewart A. et al., "Preparation and characterisation of biodegradable starch-based nanocomposite materials," Polymer International, 2003, pp. 1767-1773, vol. 52.

Pourjavadi, Ali et al., "Synthesis, Characterization, and Swelling Behavior of Alginate-g-Poly(sodium acrylate)/Kaolin Superabsorbent Hydrogel Composites," Journal of Applied Polymer Science, 2007, pp. 2631-2639, vol. 105, Issue 5.

De Carvalho, A.J.F. et al., "A first insight on composites of thermoplastic starch and kaolin," Carbohydrate Polymers, 2001, pp. 189-194, vol. 45.

Duan, Wengui et al., "Preparation and characterization of the graft copolymer of chitosan with poly[rosin-(2-acryloyloxy)ethyl ester]," Carbohydrate Polymers, 2008, pp. 582-586, vol. 73.

El-Zahhar, A.A. et al., "Gamma Radiation-Induced Preparation of Polymeric Composite Sorbents and Their Structure Assignments," Journal of Macromolecular Science, Part A: Pure and Applied Chemistry, Feb. 7, 2007, pp. 215-222, vol. 44:2.

Park, Hwan-Man, et al., "Envirnomentally friendly polymer hybrids, Part 1 Mechasnical, thermal, and barrier properties of thermoplastic starch/clay nanocomposites," Journal of Materials Science, 2003, pp. 909-915, vol. 38.

Ray, Suprakas Sinha et al., "New polylactide/layered silicate nanocomposites. 5. Designing of materials with desired properties," Polymer, 2003, pp. 6633-6646, vol. 44.

Xu, Y.X. et al., "Chitosan-starch composite film: preparation and characterization," Industrial Crops and Products, 2005, pp. 185-192, vol. 21.

Wang, S.F. et al., "Biopolymer chitosan/montmorillonite nanocomposites: Preparation and characterization," Polymer Degradation and Stability, 2005, pp. 123-131, vol. 90.

Wiesbrock, Frank et al., "Microwave-Assisted Polymer Synthesis: State-of-the-Art and Future Perspectives," Macromol. Rapid Commun., 2004, pp. 1739-1764, vol. 25.

Theng, B. K. G., "Clay-Polymer Interactions: Summary and Perspectives," Clays and Clay Minerals, 1982, pp. 1-10, vol. 30, No. 1.

Gao, Deyu et al., "Superabsorbent Polymer Composite (SAPC) Materials and their Industrial and High-Tech Applications," Tag der Verleihung, Feb. 28, 2003, pp. 1-137.

Pourjavadi, A. et al., "Chitosan-g-Poly(Acrylic Acid)Kaolin Superabsorbent Composite: Synthesis and Characterization," Polymers & Polymer Composites, 2006, pp. 203-211, vol. 14, No. 2.

* cited by examiner

Fig 1

SEM analysis

Figure 2:
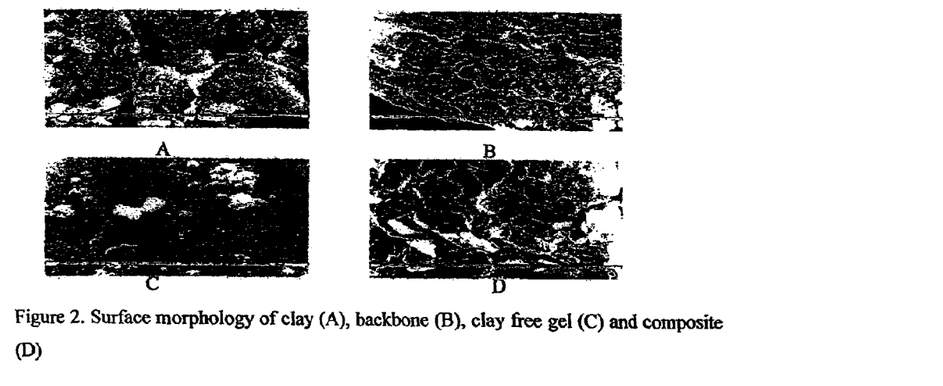
FIG. 2. depicts the surface morphology of clay, backbone, clay free gel and composites of various clay ratios and depicts surface morphology of clay (A), backbone (B), clay free gel (C) and composite (D).
Figure 3:
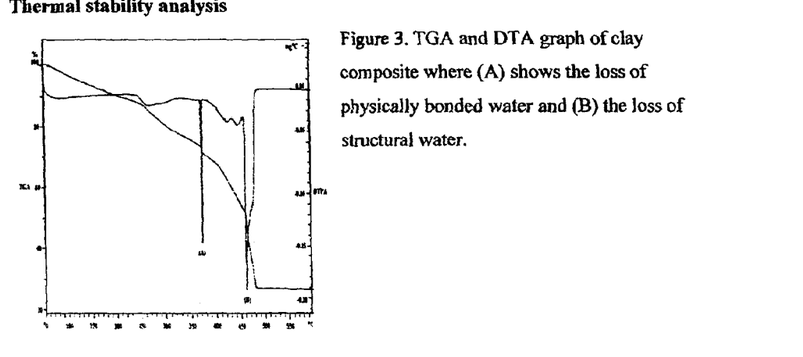
FIG. 3. Thermo Gravimetric Analysis (TGA) and Differential Thermal Analysis (DTA) graph of clay composite where (A) shows the loss of physically bonded water and (B) the loss of structural water.

Figure 2 depicts the surface morphology of clay, backbone, clay free gel and composites of various clay ratios.

Figure 2. Surface morphology of clay (A), backbone (B), clay free gel (C) and composite (D)

Thermal stability analysis

Figure 3. TGA and DTA graph of clay composite where (A) shows the loss of physically bonded water and (B) the loss of structural water.

SUPERABSORBENTS AND THE METHOD(S) OF OBTAINING THE SAME

FIELD OF INVENTION

This invention relates to novel non-composite and composite superabsorbents and the method(s) of obtaining the same.

BACKGROUND OF INVENTION

Superabsorbent polymers (SAPs) or hydrogels or hydrocolloids are capable of absorbing many times their own weight of fluids such as water and retain it under moderate pressure. These materials are of diverse chemical origins as recognized in the prior art. Owing to their ability to absorb fluids, they find extensive use in sanitary products including baby napkins, meant to absorb baby urine and faecal moisture; female sanitary pads meant to absorb menstrual fluid and others. Superabsorbent polymers absorb more than 80 g of water per gram of the xerogel (dry polymer), unlike the common absorbent materials (Table 1).

TABLE 1

Water absorbency of some common absorbent materials in comparison with an indigenous SAP sample

| Absorbent material | Water absorbency (%) |
| --- | --- |
| Whatman No. 3 filter paper | 180 |
| Facial tissue paper | 400 |
| Soft polyurethane sponge | 1050 |
| Cotton Ball | 1200 |
| Pusa Hydrogel | >35,000 |

Water absorption capacity (WAC) is the most important characteristic of the superabsorbent polymers. There are many ways to measure WAC, though there is no accepted standard yet. Usually, it is measured using volumetric or gravimetric or spectroscopic or microwave method. The volumetric method measures the volume change of SAP (or the water) before and after the absorption, the gravimetric method measures the weight change of SAP, the spectrometric method measures the change in the UV-spectrum of the SAP and the microwave method measures the microwave absorption by energy changes.

The WAC of a SAP depends upon its composition and structure generated by the preparation method, as well as the presence of electrolytes in water. For example, the WAC of SAP can be several thousand grams water per gram SAP when in contact with pure water, but in water containing urine, blood, metal ions etc., it will be reduced by several folds the maximum value in pure water. Water absorbed in the SAP can exist as bound water, half-bound water and free water. Free water shows a freezing point when the environment temperature touches around 0° C., however, this freezing point cannot be noticed with the bound water. The half-bound water shows property in between. The bound water in SAP usually is 0.39-1.18 g per g. Most water in the SAP is free water. Tatsumi studied the effect of chemical structure on the amount of microwave absorption of water in various polymer films at 9.3 GHz. The absorption was directly proportional to both the volume increase of the sample film and the amount of water in the polymer. The principle of water absorption by polymer can be illustrated by the Flory theory of an ionic network.

$$Q^{5/3} = \{(1/2 \times I/Vu \times 1/S^{1/2}) + (1/2X1)/V_1\} \times V_0/v$$

Where Q=maximum swelling ratio of SAP, I=electronic charge on the polymer structure per polymer unit, Vu: polymer repeating unit volume, S=ionic strength of solution, $X_1$=interaction parameter of polymer with solvent, $V_1$=molar volume of solvent, in a real network, $V_0$=unswollen polymer volume, v=effective number of chains. These parameters in the equation formed a balance of the swelling which can be further defined as follows: $1/2 \times I/Vu \times 1/S^{1/2}$ denotes ionic strength on both polymer structure and in the solution, $(1/2 \cdot X_1)/V_1$ denotes the affinity of network with solvent; $V_0/v$ is cross-linking density. The equation shows that the water absorption is a function of osmotic pressure, the affinity of water and polymer, and the cross-linking density of the network.

The swelling process of SAP can be explained as follows: the solvent tries to penetrate the polymer networks and produce a 3D-molecular network, expanding at the same time, the molecule chain between the crosslinked points, thus decreasing the configuration enthalpy. The molecular network has an elastic contractive force which tries to make the networks contract. When these opposed forces reach equilibrium, the expansion and contraction reach a balance too. In this process, the osmotic pressure is the driving force for the expansion of swelling, and the network elastic force is the driving force of the contraction of the gel.

These materials find important application in agriculture as water retaining soil conditioners, a use that is likely to catch up as water is recognized to become the most valuable and scarce commodity in future. The technologies and products that conserve and promote its judicious and efficient use are likely to be sought after in the future.

The term soil conditioner implies compounds, which favourably alter the physical and/or chemical properties of soil. The concept of using polymer materials as soil conditioners is not new. Natural polymers such as polyuronic acids, alginic acids, agar, gum, pectin, starch, etc. have been successfully used in the past for soil conditioning. However, their easy biodegradation and low water holding property are bottlenecks in practical use.

Purely synthetic SAPs include polyacrylates, sulfonated polystyrene, polyvinyl alcohol, polyethylene oxides, polyvinylpyrrolidone, polyacrylonitriles, polyacrylamide and the like. Some of these like polyacrylamide have been used for water retention purposes in agriculture.

Scale of performance and economic considerations have evoked interest in the development of SAPs and SAP composites. Superabsorbent composites based on natural raw materials and clay minerals, which can be chemically entangled with hydrophilic units of synthetic superabsorbent polymers to yield products with superior water holding characteristics and the desired persistence will go a long way in improving their application prospects in future agriculture. A need also exists for a superabsorbent material which combines the advantage of liquid absorption potential of conventional SAPs, advantageous liquid distribution properties of biopolymer and permeability and mechanical stability of clay minerals, by virtue of which the resultant hydrogels do not form soft gelatinous masses when hydrated, have good absorbent properties, gradual releasing potential and controlled biodegradability. Moreover, there is a need for a simple, convenient and inexpensive method for making such materials, the aspects that have been explored in this invention Variety of superabsorbent polymers have been developed following different procedures and used under diverse use situations. U.S. Pat. No. 3,669,103 discloses a process for acrylic acid and acrylamide based gelling polymers for use in personal care products. U.S. Pat. No. 6,500,947 describes a method of making superabsorbent hydrogel from cellulose fibres obtained from wood pulp, by sulfonation of the fibres. However, the use of sulfuric acid renders the hydrogel mechanically unstable resulting in soft gelatinous mass on exposure to water, making it difficult to handle in practice.

In U.S. Pat. No. 4,244,880, hydrogels meant for temperature controlled solute delivery system in human body include crosslinked poly N-isopropylacrylamide and crosslinked cellulose ether gels. The method used involves exposure of the reaction mixture to nitrogen atmosphere containing less than 2% oxygen. Another example of such hydrogels is provided in U.S. Pat. No. 5,064,653, which describes hydrophilic foam compositions containing hydrogels belonging to the category of starch grafted on copolymers of acrylamide salts, acrylate salts and mixtures thereof. Hydrophilic properties of carboxymethyl cellulose have been utilized in the U.S. Pat. No. 3,586,648 in treatment of polyurethane foams in such a manner as to render the latter hydrophilic.

Use of crosslinked polyacrylamides in plant growing media is well established. U.S. Pat. No. 4,579,578 describes free radical polymerization of acrylamide in the presence of N, N-methylene bisacrylamide resulting in a hydrogel capable of absorbing 30 times its own volume of water.

Similar plant growth compositions are described in U.S. Pat. No. 4,559,074 wherein crosslinked non-ionic polyacrylamide has been incorporated into the porous growth medium. Yet another evidence of the versatile potential of carboxymethyl cellulose is provided by U.S. Pat. No. 6,387,978 reporting preparation of crosslinked carboxymethyl cellulose involving ionic crosslinking by anions or metal cations, non-ionic crosslinking by chemical crosslinking agent or high energy gamma radiations.

Similar type of polyacrylamide absorbent materials are known in the art and are described in U.S. Pat. Nos. 4,102,340; 3,229,769; 3,670,731 and Indian Patent Application No. 3462/DEL/2005. The polymerization techniques for the aforesaid materials include the use of anionic peroxide catalysts, photopolymerization with a riboflavin activator and the like.

Clay-polymer composites are also attracting ever increasing attention in recent years (Theng, 1974). Traditionally, clays have been used as fillers for improving a material's physico-chemical properties and reducing product cost. In 1985, an inorganic-organic composite (Superabsorbent Polymer Clay Composite, SAPC) was prepared by intercalating acrylamide into an expandable smectitic clay, such as bentonite using γ-ray radiation-induced polymerization (Rong et al, 1985). The preparation technique was improved and some of the properties of the composite material reported (Gao, 1993). The new material showed good absorption capacity to water and its vapours. The material also showed an interesting physico-chemical and electromechanical reaction to environmental changes such as temperature, moisture, electric fields, concentration changes of chemical species, and pH (Gao and Heimann, 1993) and has been used in oil fields for enhanced oil recovery processes and in other areas such as agriculture, forestry etc.

Figure 1:
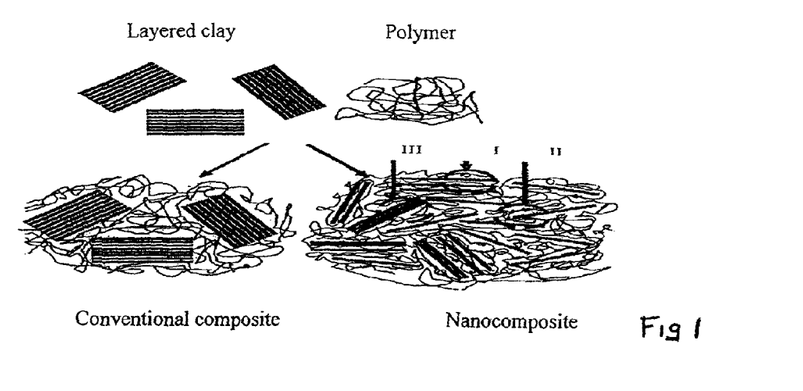
FIG. 1. shows difference between a conventional composite and a nancomposite.

When layered clays are filled into a polymer matrix, either conventional composite or nanocomposite is formed depending on the nature of the components and processing conditions. Conventional composite is obtained if the polymer can not intercalate into the galleries of clay minerals. The properties of such composites are similar to that of polymer composites reinforced by micro particles. As shown in FIG. 1, two types of nanostructures result from the mixing of clay minerals and a polymer depending on the reaction conditions. One is the intercalated nanocomposite (I), in which monolayer of extended polymer chains is inserted into the gallery of clay mineral resulting in a well ordered multilayer morphology stacking alternately the polymer layers and clay platelets with a repeating distance of a few manometers. The other is exfoliated or delaminated nanocomposite (II), in which the clay platelets are completely and uniformly dispersed in a continuous polymer matrix. In most cases, a cluster (the so-called partially exfoliated) nanocomposite (III) is common in polymer nanocomposites.

Of late, biopolymers are receiving growing interest due to environmental concerns, increasing prices of crude oil and global warming. These polymers are naturally occurring, being of plant or animal origin. Numerous biopolymers such as starch, chitosan, derivatives of alginic acid, carrageenan, polylactic acid, cellulose and its derivatives, rubber etc. have been exploited to synthesize biopolymer based composites/nanocomposites (Chang et al, 2003; Mathew et al, 2005; Wu et al, 2004; Kvien et al, 2005; Mathew et al, 2006; Ray et al, 2003; Carvalho et al, 2001; McGlashan and Halley, 2003; Park et al, 2003; Wang et al, 2005; Xu et al, 2005; Pourjavidi and Mandavivia, 2006; Pourjavidi et al, 2007).

Synthesis of superabsorbent hydrogels using conventional heating is increasingly being replaced by greener techniques such as microwave assisted polymerization (Singh et al, 2004; Singh et al, 2005; Duan et al, 2008). However, such techniques have not been tried as yet in the synthesis of superabsorbent composites.

OBJECTS OF INVENTION

The main object of this invention is to develop novel superabsorbents on biopolymers of plant origin.

Other object of this invention is to develop novel superabsorbents both noncomposites, particularly bioxerogels and composites, particularly bio nanocomposites.

Another object is to develop novel superabsorbents, which are grafted and cross-linked with ethylenically unsaturated monomers and intercalated with clay minerals in a homogeneous polar medium.

Yet another object is to develop novel superabsorbents involving simple and energy efficient green methods and green chemistry.

Further object is to develop novel superabsorbents which involve in situ grafting and cross-linking of backbone with water-soluble ethylenically unsaturated monomers, with or without clay intercalation in polar medium.

STATEMENT OF INVENTION

This invention relates to novel non-composite and composite superabsorbents, wherein the dry superabsorbents are xerogels, more particularly the bio-xerogels or the composites, particularly the biocomposites, more particularly the bionanocomposites and the method(s) of obtaining the same characterized by simultaneous in situ grafting and cross linking of ethylinically unsaturated monomers on to a single biopolymer of plant or animal origin, or on combination of different biopolymers or biopolymer(s) or/and clay(s), in a homogeneous polar phase, in the presence of initiator and crosslinker of chemical or non-chemical origin, at a temperature of 40 to 90° C., achieved by conventional or microwave heating, reaction time varying from instantaneous to 48 hours, involving use of alkali, either in situ or post reaction at room or elevated temperatures for achieving superior absorbency, in an inert or ambient reaction environment, to yield a neutral or near neutral product.

DETAILED DESCRIPTION OF INVENTION

This invention relates to novel superabsorbents based on biopolymer/s of plant origin, both noncomposites, particularly bioxerogels, and composites, particularly the nanocomposites, more particularly the bionanocomposites, grafted and crosslinked with ethylenically unsaturated monomers and intercalated with clay mineral/s in a homogeneous polar medium. It describes simple and energy efficient green method/s involving green chemistry, of preparing the superabsorbents, which involve(s) in situ grafting and crosslinking of backbone with water-soluble ethylenically unsaturated monomer/s, with or without clay intercalation in polar medium.

This invention relates to novel non-composite and composite superabsorbents and method(s) of obtaining the same, characterized by simultaneous in situ grafting and cross linking of ethylinically unsaturated monomers on to single biopolymer of plant or animal origin, or on combination of different biopolymers or biopolymer(s) or/and clay(s), in a homogeneous polar phase, in the presence of initiator of chemical or non-chemical origin and crosslinker, at a temperature of 40 to 90° C., achieved by conventional or microwave heating, reaction time varying from instantaneous to 48 hours, involving use of alkali, either in situ or post reaction at room or elevated temperatures for achieving superior absorbency, in an inert or ambient reaction environment, to yield a neutral or near neutral product for diverse applications, either as such or in combination with various other input-products.

It also describes simple and energy efficient green method(s) of preparing the superabsorbents, which involve(s) in situ grafting of backbone, with water-soluble ethylenically unsaturated monomer(s) through simple chemical reaction or clay intercalation in polar medium. In a preferred embodiment, the superabsorbents are formed from ethylenically unsaturated monomer(s) comprising either of an acrylamide, acrylonitrile, acrylamido-propanesulfonic acid, acrylic acid, acrylate, N-vinyl pyrrolidone or the like, used at a concentration ranging from 3-85% on mass-by-mass basis of the backbone mass, preferably from 10 to 70%, grafted and simultaneously crosslinked on to a biopolymer backbone, not limited to but exemplified by *Sterculia urens, Cochlospermum religiosum*, guar gum, tragacanth gum, *Acacia* gum, cellulose, modified cellulose, starch, modified starch, alginic acid and for its derivatives, and for a 1:1 and/or for 2:1 clay exemplified by kaolinite, halloysite, endalite, montmorillonite, beidellite, nontronite, talc, mica, vermiculite, illite, bentonite, chlorite and the like, used either alone or in combinations, using a crosslinker exemplified by glutaraldehyde, adipic acid, dihydrazide, bisacrylamides etc. at a concentration of 0.05-10% on mass-by-mass basis of the weight of the reaction mass, preferably at 1 to 3.5 percent, all homogenized in a polar solvent such as water, methanol, ethanol, propanol and the like, either alone or in mixtures; more preferably water alone and heated at a preferable temperature of 25 to 100° C. either conventionally or using microwave irradiation in the presence of an initiator comprising any of the water soluble persulfates, ammonium cerric nitrate, peroxides such as hydrogen peroxide or organic peroxides, water soluble azo compounds such as 2,2'-azobis-(2-amidinopropane) and the like, either alone or in combination with a co-initiator, used at a concentration of 0.005 to 6.5%, preferably from 0.01 to about 5% on mass by mass basis of the total reaction mass, or electromagnetic radiation exemplified by gamma rays, high energy ultraviolet rays and the like, in an inert or ambient reaction environment, preferably ambient environment to achieve the gel point in a time period of instantaneous to 24 hours followed by hydrolysis using alkali. The hydrolysis in the present invention is in situ or post grafting, preferably post grafting.

The superabsorbents of the present invention have high water absorptive property relative to known materials, of the order of at least 15000% and 50,000% respectively of non-composites and the composites, on mass-by-mass basis of the dry superabsorbent mass. The hydrogels obtained from the non-composite and composite superabsorbents of the present invention remain intact, even at temperatures above 50° C. These do not present any undesirable risk to soil environment owing to their controlled biodegradation over time unlike the known non-biodegradable hydrogels used in agriculture.

The present invention relates to novel superabsorbents, both non-composite and composite(s) including the bio-nanocomposite(s) and method(s) of obtaining the same, characterized by simultaneous grafting and crosslinking of ethylenically unsaturated monomer(s) onto the backbone biopolymer and/or the clay in the presence of initiator(s) and crosslinker(s) in a homogeneous phase in polar solvent(s) at a temperature of 25-100° C., reaction time to achieve the gel point from instantaneous to 24 hours and an inert or ambient reaction environment.

The hydrogels obtained by following the procedure(s) described herein have grafting efficiency of the order of greater than 70%, a free swell capacity of greater than 15000% and 50000% for non-composite and composite superabsorbents(s) respectively in distilled water, and of more than 7000% in ionic solutions preferably those containing $NH_4^+$, $NO_2^-$, $NO_3^-$ ions and the like.

As used herein and in the claims, the singular forms 'a', 'an' and 'the' include plural reference unless the context clearly dictates otherwise.

The hydrogels of the present invention preferably possess highly desirable water sorptive characteristics. For example, the hydrogels herein preferably have high grafting efficiency values. The grafting efficiency is a measure of how efficiently the ethylenically unsaturated monomer is grafted onto the backbone.

The superabsorbents of the present invention have remarkably high water absorption potential expressed as $Q_{H2O}$, from about at least 2000% to more than 1,00,000%, this being expressed in the pH range 4-9, preferably >2000% at pH 4.0, more preferably >4000% at pH 9.0 and most preferably greater than 15000% at pH 7.0. Percent swelling is computed as follows:

$$QH_2O = \frac{\text{(Weight of swollen material} - \text{weight of dry sample)}}{\text{Weight of dry sample}}$$

This may also be expressed as free swell. The free swell measures the ability of a polymer to absorb fluid, preferably water without being subjected to a confining or restraining pressure. In the present invention, free swell is preferably determined by gravimetric method described in one of the examples provided herein.

The superabsorbents of the present invention possess granular texture, making them potential candidates for use in diverse areas. These are insoluble in water but swell with a high rate of expansion. These are preferably prepared by a process which may include but preferably not require any inert atmosphere, without affecting adversely the degree of swelling of the resulting product. The structure of the gel also remains intact.

The superabsorbents of the present invention also preferably have a residual moisture retention potential of the order of >10% on mass-by-mass basis at 15 bars pressure. The residual moisture retained, as measured in the present invention by pressure plate membrane apparatus, points towards the ability of the material to retain fluid preferably water/ionic solution against different pressure gradients as equivalent to the stress levels generated in plant-soil systems.

The process of the present invention has a number of advantages over known processes. For example, one of the preferred steps in the present invention involves the use of limited amount of water i.e. at high consistency, yet achieving high water absorbency. Another novelty lies in the fact that the reaction makes use of energy efficient green technique.

As used herein, the term consistency refers to the concentration of backbone polymer in the reaction mixture. As such, the consistency represents the weight of backbone polymer present in a homogenised feed divided by total weight of the feed multiplied by 100.

Backbone polymer described herein for the preparation of superabsorbents including the composite(s) is a homo/hetero-polysaccharide of natural origin (animal/plant), preferably of plant origin, exemplified by, *Sterculia urens, Cochlospermum religiosum,* guar gum, tragacanth gum, *Acacia* gum, cellulose, modified cellulose, starch, modified starch, alginic acid and/or its derivatives and the like, used alone or in combinations.

The biopolymer used in the present invention has been characterized by FT-IR and solid state $^{13}C$ NMR as having OH and/or COOH groups. The backbone contains in its structure at least one or more monosaccharide unit(s) out of glucose, fructose, galactose, rhamanose, galacturonic acid, and the likes.

It is preferred in the present invention that the ethylenically unsaturated monomer contains at least one carboxamide group. Suitable ethylenically unsaturated monomers are acrylic monomers. Particularly preferred monomers include such specific compounds as acrylamide, methacrylamide, N-methacrylamide, N-ethacrylamide, N-isopropylacrylamide, diacetoneacrylamide, 2-acrylamido-2-methyl-1-propanesulfonic acid and its salts, and the likes. Acrylonitrile, methacrylonitrile and the likes are also suitable for use as ethylenically unsaturated monomers.

The ethylenically unsaturated monomer may further contain an acid moiety. Such monomers are also well known in the art and include such specific compounds as acrylic acid, methacrylic acid, ethacrylic acid, α-chloroacrylic acid, α-cyanoacrylic acid, vinyl sulfonic acid, acrylamidopropanesulfonic acid, crotonic acid, acryloxypropionic acid, and the likes.

The more preferred ethylenically unsaturated monomers include acrylamide, methacrylamide, acrylonitrile, acrylic acid, methacrylic acid, alpha-cyanocrylic acid and acrylamide-2-methyl-1-propane sulfonic acid and its salts. Specially preferred monomers are acrylamide, acrylonitrile and 2-acrylamido-2-methyl-1-propane sulfonic acid and mixtures thereof.

Grafting may be carried out using monomer as such without recrystallization and/or neutralization or it may be recrystallized and/or neutralized, completely or partially, prior to mixing with the backbone polymer. Preferably, the monomers are used as such. Grafting efficiency may be lowered if the acid monomers are neutralized prior to grafting.

Compounds that are used to neutralize the acid group include those which do not have any adverse effect on the grafting process, yet they sufficiently neutralize the acid. The amount of monomers in the reaction mixture can be such as to be suitable to result in hydrogels having superabsorbent properties, as well as other desirable characteristics described herein. It is preferred that the amount of monomers used in the present invention be within the range from about 3% to 85% by weight based on the total weight of reactants. Preferably, the amount is within the range of about 10 to 70%, based on the mass of the backbone.

It is preferred in the present invention that the reaction is free radical initiation polymerization, using initiator which may or may not be of chemical origin. Suitable chemical free radical initiators used in the present invention include, for example ammonium cerric nitrate, water soluble persulfates such as sodium persulfate, ammonium persulfate, potassium persulfate, and other alkali metal persulfates, hydrogen peroxide, organic peroxide, water soluble azo compounds such as 2,2'-azobis-(2-amidinopropane) and the like. Some of these initiators may or may not be combined with the co-initiators.

For example, persulfates may be combined with tetramethyl ethylene diamine or used as such. Hydrogen peroxide may be combined with iron, sulfites or amines to initiate the grafting reaction or may be used as such under mild alkaline conditions and reduced pressure. Non-chemical means of initiation may include electromagnetic radiation such as gamma rays, high-energy ultraviolet rays and the like.

The total amount of initiators used may range from about 0.005 to about 6.5%, preferably from 0.01 to about 5% and more preferably from 0.5 to 4.0% on mass-by-mass basis of the total reaction mass.

In order to obtain hydrogels of very high absorbancy and to render them water insoluble, the grafting of monomer on to the backbone is achieved in the presence of chemical crosslinker. Crosslinking agents used in the present invention include those having polyfunctional groups capable of creating inter- and intra-crosslinks between backbone and grafted chains.

The crosslinking agent is used in an amount that affords hydrogel with desired crosslinking density. Preferably, the crosslinking agent is used in an amount ranging from 0.01-10% based on the total weight of the reaction mass. More preferably, the amount of crosslinking agent varies between 0.05 to 3.5 percent. It is observed in the present invention that use of more than 4% crosslinker on weight basis leads to products with lower absorbancy but equilibration swelling time is attained at a faster rate.

Polyfunctional crosslinking agent(s) preferably used in the present invention is(are) selected from among glutaraldehyde, adipic acid dihydrazide, bisacrylamides such as N,N-methylenebisacrylamide, N, N-ethylenebisacrylamide N, N-dihydroxyethylenebisacrylamide, divinylsulfone and the like and/or the mixtures thereof.

One or more (in combination) clay mineral(s) used in the present invention belong to any one or more of the following groups:

1:1 such as kaolinite, halloysite, endalite; 2:1 such as montmorillonite, beidellite, nontronite, talc, mica, vermiculite, illite, bentonite; 2:2 such as chlorite and the like.

The particle size of the clay used in the present invention for intercalation/exfoliation lies in the range of <5.0 μm, preferably 0.5-3.0 μm, more preferably <0.1-2.0 μm.

The crosslinking agents preferably used in the present invention are typically soluble in water at a temperature ranging from 5-100° C., preferably from 10-80° C., more preferably from 15-40° C.

The products obtained above in the present invention may be subjected in situ or before final processing, to at least partial hydrolysis with the hydrolyzing agent. In one embodiment, the hydrolyzing agent is a base such as, for example, aqueous solution of sodium or potassium hydroxide, sodium carbonate or sodium bicarbonate and the like. The hydrolyzing agent employed in the present invention has a preferable concentration in the range of 0.1-5N, more preferably 0.2-2N.

Another preferred embodiment describes the method of preparation of the superabsorbent materials of the present invention.

In one embodiment of the method, the monomer is grafted onto backbone material preferably in presence of crosslinker and initiator.

For effective solvation, the backbone can be swelled in a suitable solvent, preferably polar solvent such as methanol, ethanol, water; more preferably water to achieve better grafting efficiency. The consistency of the feed is kept below 20%, preferably below 17% and more preferably in the range 3%-15%. For efficient composite formation, the clay mineral is added either with backbone or prior to its addition and allowed to swell.

In another embodiment, the gel formation is facilitated by conventional heating or microwave exposure. The reaction temperature as well as the reaction period will depend on the amount of initiator and the technique used to attain the gel point. For example, the reaction temperature generally employed in the present invention lies in the range 15°-100° C., preferably 20°-80° C. and more preferably 25° to 60° C. In the present invention, the time required for gel setting ranges from instantaneous to 24 hours, more preferably 30 seconds to two hours.

The composites obtained in the present invention may or may not employ a surfactant; preferably the synthesis is achieved without use of surfactants.

Amount of solvent present in the feed influences the grafting efficiency. In one embodiment, the quantity of solvent per unit reaction mass is preferably at least 1 ml g$^{-1}$.

For effective swelling the composite of the present invention can be allowed to swell in aqueous alkali solution for a time period ranging from 30 minutes to 48 hours at temperature ranging from 25-100° C.

In another embodiment, the hydrolysis can be carried out under in situ conditions during polymerization and intercalation process or post grafting. It is preferably carried out post grafting.

The polymerization in the present invention can be carried out in inert atmosphere or under ambient environment. Reaction vessels used in the present invention include simple glass wares such as beakers or other similar containers, depending on the batch size.

The composites so obtained are processed following appropriate workup procedures as known in the art.

Recovery of the xerogel in the present context means that all of the water present in the hydrogel is removed therefrom. The non-composites and the composites of the invention can be dried by precipitating the gel in a dehydrating solvent like acetone, methanol, ethanol, propanol and the like.

The recovered xerogel may still contain traces of water, which may remain entrapped in the inner matrix of the polymer. Preferably, the amount of this water is <50% on weight basis of the grafted hydrogel, more preferably <25%, and most preferably <10 percent.

EXAMPLES

The invention will be illustrated but not limited by the following examples. Those skilled in the art recognize that various modifications can be made to the invention without departing from the spirit and scope thereof.

Example 1

Preparation of a Representative Non-Composite Superabsorbent Hydrogel

A representative method for preparing a representative non-composite xerogel is described.

The biopolymer was subjected to swelling in an aqueous solution of an acrylamide and a bisacrylamide in a glass beaker. Consistency of the feed was kept at 4%. The reaction mixture was heated to attain temperature in the range of 40-90° C. using a thermostat controlled water bath/microwave irradiation. Persulphate-biopolymer mixture was added. Alkali solution was added after gel formation. Excess alkali was removed to attain the desired pH. The gel was dried as such or after precipitation in a dehydrating solvent, in an oven at 50° C. or in open air. The % add-on was 100%.

Example 2

Preparation of a Nanocomposite

A representative method for preparing a nanocomposite is described. The composite is prepared by swelling the mixture of biopolymer and clay (1:1 or 2:1 type) in the ratio ranging from 1:005 to 1:1, on weight basis, in an aqueous solution of one of the vinyl monomers mentioned in detailed description and a polyfunctional crosslinker, in a glass beaker. The reaction mixture was heated to attain temperature in the range of 40-90° C. using a thermostat controlled water bath/microwave irradiation.

Chemical initiator—an inorganic persulphate was introduced in clay-biopolymer mixture. Gel formed was immersed in an alkali solution. Excess alkali was removed to attain the desired pH. The gel was dried as such or after precipitation in a dehydrating solvent, in an oven at 50° C. or in open air. The % add-on was (10.00-368.00%). Effect of variation of backbone-clay/monomer ratio on percent add-on is shown in Table 2.

TABLE 2

Effect of variation of backbone biopolymer - clay: monomer on per cent add-on

| Sample number | % Add-on |
|---|---|
| A (1:0.50) | 53 |
| B (1:0.67) | 112 |
| C (1:1.33) | 205 |
| D (1:2.00) | 146 |

Example 3

Total Absorptive Capacity Determination Test

A method for determining the total absorptive capacity of composites as used in the present invention is described.

Sieve method was used in the present invention to measure the water absorption potential of the composite(s) as a function of backbone: clay ratio, clay type, vis-a vis monomer concentration, crosslinker and initiator content, quantity of water per unit reaction mass. Xerogel or the dry composite (0.1 g, dry weight basis) was immersed in 100 ml to 500 ml distilled water taken in a beaker. The swelling was allowed for twenty four hours at 25 and 45° C., separately. The gels were then filtered through plastic sieves till complete drainage of free water. Extra water was wiped off and the sieve along with the gel mass was weighed. The amount of distilled water per gram of dry superabsorbent material was calculated using the following expression:

$$H_2O(g/g) = \frac{(\text{Weight of swollen material} - \text{weight of dry sample})}{\text{Weight of dry sample}} \times 100$$

Representative results of some composites are summarized in Tables 3-8.

TABLE 3

Effect of variation of backbone biopolymer - clay: monomer ratio on water absorptive capacity

| | $H_2O(g/g)$ | |
|---|---|---|
| Sample number | 25° C. | 45° C. |
| A (1:0.50) | 68.20 | 102.50 |
| B (1:0.67) | 127.60 | 165.40 |
| C (1:1.33) | 172.40 | 208.3 |
| D (1:2.00) | 110.50 | 167.6 |

TABLE 4

Effect of clay content on the water absorbency of nanocomposites

| | Mean water absorption $(g\ g^{-1})$ | |
|---|---|---|
| Clay percentage (wt %) | 25° C. | 45° C. |
| 0.0 | 168.3[a] | 171.23[a] |
| 3.0 | 170.50[a] | 172.32[a] |
| 9.0 | 145.90[b] | 146.10[b] |
| 15.0 | 138.10[c] | 140.33[c] |
| 18.0 | 102.30[e] | 119.93[d] |
| 24.0 | 89.77[f] | 98.70[e] |

TABLE 5

Effect of alkali strength on water absorptive capacity (g/g) of representative composites

| Alkali conc. | Temperature | Mean |
|---|---|---|
| 0.1N | 25° C. | 238.23 |
|  | 45° C. | 263.76 |
| 0.5N | 25° C. | 590.00 |
|  | 45° C. | 840.00 |
| 1N | 25° C. | 504.57 |
|  | 45° C. | 593.60 |
| 1.5N | 25° C. | 540.33 |
|  | 45° C. | 566.13 |
| 2N | 25° C. | 451.70 |
|  | 45° C. | 479.66 |

TABLE 6

Comparison of water absorptive capacities of composites in distilled water formed under nitrogen atmosphere (A) and open air (B)

| | $QH_2O(g/g)$ | |
|---|---|---|
| Sample number | 25° C. | 45° C. |
| A | 743.20 | 730.00 |
| B | 590.00 | 840.00 |

Example 4

Water Absorptivity Under Various Environments

In this example, swelling behaviour of a representative superabsorbent as a function of external environment namely pH of solution, temperature and time of exposure, salt type and the strengths of their solution, as studied in the present invention, is reported.

Sieve method as mentioned in example 3 was used, to measure the water absorbency. The results of some representative composites are summarized in Tables. 7-9.

TABLE 7

Effect of pH on water absorbency

| pH | $QH_2O\ (g/g)$ |
|---|---|
| 4 | 58.33 |
| 7 | 777.66 |
| 9 | 151.11 |

TABLE 8

Effect of temperature and time of exposure on water absorbency

| Time (hr) | Temperature (° C.) | Mean |
|---|---|---|
| 2 | 25 | 298.33 |
|   | 35 | 311.73 |
|   | 45 | 320.6 |
| 4 | 25 | 444.53 |
|   | 35 | 667.04 |
|   | 45 | 495.2 |
| 8 | 25 | 468.17 |
|   | 35 | 750.00 |
|   | 45 | 854.00 |
| 12 | 25 | 746.30 |
|   | 35 | 746.30 |
|   | 45 | 854.00 |
| 24 | 25 | 740.00 |
|   | 35 | 740.00 |
|   | 45 | 854.58 |

TABLE 9

Effect of salt type and strength on water absorbency

| Salt type | Concentration (mM) | $QH_2O$ (g/g) |
|---|---|---|
| $(NH_4)_2SO_4$ | 5 | 217.98 |
|  | 10 | 174.50 |
|  | 15 | 153.44 |
|  | 20 | 138.12 |
| $NH_4NO_3$ | 5 | 212.47 |
|  | 10 | 164.02 |
|  | 15 | 139.57 |
|  | 20 | 132.48 |
| $KNO_3$ | 5 | 221.53 |
|  | 10 | 179.07 |
|  | 15 | 149.55 |
|  | 20 | 140.73 |
| NaCl | 5 | 197.68 |
|  | 10 | 181.25 |
|  | 15 | 157.97 |
|  | 20 | 135.48 |
| Urea ($NH_2CONH_2$) | 5 | 380.28 |
|  | 10 | 361.55 |
|  | 15 | 353.13 |
|  | 20 | 353.57 |
| Distilled water | — | 740.00 |

Example 5

Green Chemistry Parameters

In this example, a comparison of conventional and microwave assisted techniques of synthesis as used in the present invention is presented (Table 12) ? 10

TABLE 10

Comparative efficiency of process parameters

| Parameter | Conventional synthesis | Microwave synthesis | Improvement |
|---|---|---|---|
| Overall Yield (%) | 50.317 | 77.439 | 27.122% increase |
| E (Environmental factor) (Kg waste/Kg product) | 0.987 | 0.2913 | 69% reduction |
| Carbon Efficiency (%) | 32 | 49.3 | 17% increase |

Various parameters as depicted in the example are defined as follows:

Environmental (E) factor: The E-factor is the ratio of the mass of waste per unit of product.

E-factor=Total waste (Kg)/Total product (Kg)

Carbon Efficiency: Carbon efficiency is a simplified formula developed at GlaxoSmithKline (GSK).

The mathematical representation is shown below:

$$\text{Carbon Efficiency (\%)} = \frac{\text{Amount of carbon in product}}{\text{Total carbon in Reactants}} \times 100$$

Example 6

Characterization of Superabsorbents

In this example, FT-IR, $^{13}$C solid state NMR, X-ray diffraction and scanning electron microscopic analyses of a representative nanocomposite of the present invention are described. Thermal stability was studied by Thermo Gravimetric Analysis (TGA).

FT-IR

Table 11 describes the bands characteristic of functional groups present in backbone, clay, clay free gel and the composite.

TABLE 11

FTIR bands of backbone, clay, clay free gel and composite

| Material | Wavelength ($cm^{-1}$) | Functional group |
|---|---|---|
| A) Backbone | 3650.25 | O—H stretching |
|  | 2940.04 | C—H stretching |
|  | 1728.48 | Carbonyl stretching of —COOH |
|  | 1416.83 | C—O stretching of —COOH |
|  | 1378.26 | O—H bending of —COOH |
|  | 1072.53 | C—O stretching of C—OH (overlapping C—O—C asymmetric stretching of ether) |
| B) Clay | 3699.27 | Basal O—H stretching |
|  | 3623.46 | Interlattice O—H stretching |
|  | 1030.18 | Si—O stretching |
|  | 913.88 | Basal O—H bending |
|  | 467.70 | $M^{3+}$-O vibrations |
| C) clay free gel | 2941.36 | C—H stretching |
|  | 1416.26 | —$COO^-$(as) |
|  | 1073.61 | C—O stretching of C—OH (overlapping C—O—C asymmetric stretching of ether) |
| D) Composite | 3623.45 | Interlattice O—H stretching |
|  | 2912.57 | C—H stretching |
|  | 1415.35 | —$COO^-$(as) |
|  | 1073.85 | C—O stretching of C—OH (overlapping C—O—C asymmetric stretching of ether) |
|  | 1030.00 | Si—O stretching |
|  | 480.07 | $M^{3+}$-O vibrations |

$C^{13}$ NMR

FIG. 1 depicts solid state $C^{13}$ spectra of (A) backbone (B) clay free gel and (C) composite. The peaks at 178.46 ppm, 188.571 ppm and 188.26 ppm in the spectra of A, B and C respectively correspond to carbonyl carbon of the —COOH group in A and —$COO^-$ in B and C. In backbone, a peak at 178.46 ppm confirms —COOH group. In clay free gel (B) and back bone (A), the presence of high intensity peak at 77.67 ppm can be attributed to the presence of —OH group at the monosaccharide units. However, in B and C, the intensity of this peak is less due to grafting and crosslinking of monomer on to the heteropolysaccharide leading to the formation of ether linkage which is reflected in the form of high intensity peak at ~49 ppm. The up field shift of this peak is due to presence of electron donating —COO⁻ group in its vicinity. The peak at 22.65 ppm in all the four spectra corresponds to —$CH_3$ group in the backbone.

TABLE 12

Weight loss pattern of composite as a function of temperature

| Temperature (° C.) | Weight of the composite |
|---|---|
| 54.78 | 100% |
| 98.37 | 97.07% |
| 144.69 | 93.38% |
| 192.75 | 90.16% |
| 242.10 | 87.63% |
| 292.13 | 80.89% |
| 342.39 | 75.46% |
| 393.48 | 68.15% |
| 446.01 | 57.61% |
| 493.91 | 22.10% |

We claim:

1. Non-composite and composite superabsorbents comprising 3 to 85% of ethylinically unsaturated monomers grafted and cross linked on to a combination of biopolymers or single biopolymer with at least one inorganic filler in a homogeneous polar phase in presence of 0.005 to 6.5% of a chemical initiator or a non chemical initiator and a chemical cross linker,
wherein the biopolymer is selected from *Sterculia urens, Cochlospermum religiosum*, guar gum, tragacanth gum, *Acacia* gum, cellulose, modified cellulose, modified starch, alginic acid and/or its derivatives, or combinations thereof.

2. The non-composite and composite superabsorbents as claimed in claim 1, wherein the unsaturated monomer is selected from acrylamide, acrylonitrile, acrylamido-propane sulfonic acid, acrylic acid, acrylate, or N-vinyl pyrrolidone in an amount of 10 to 70% of the mass of the backbone of the biopolymer.

3. The non-composite and composite superabsorbents as claimed in claim 1, wherein the at least one inorganic filler comprises a clay selected from kaolinite, halloysite, endalite, montmorillonite, beidellite, nontronite, talc, mica, vermiculite, illite, bentonite, chlorite or combinations thereof.

4. The non-composite and composite superabsorbents as claimed in claim 1, wherein the combination of biopolymers are prepared in the ratio of 80:20 to 50:50 of a first biopolymer to a second biopolymer.

5. The non-composite and composite superabsorbents as claimed in claim 1, wherein the combination of biopolymers and the at least one inorganic filler are prepared in the ratio of 99:1 to 1:99.

6. The non-composite and composite superabsorbents as claimed in claim 1, wherein the chemical initiator is polar solvent soluble and is selected from water soluble persulfates, peroxides, ammonium cerric nitrate, azo compounds, or combinations thereof.

7. The non-composite and composite superabsorbents as claimed in claim 1, wherein the non chemical initiator comprises electromagnetic radiation applied over a period of 0 to 24 hours, wherein the electromagnetic energy is selected from gamma rays and high energy ultraviolet rays.

8. The non-composite and composite superabsorbents as claimed in claim 1, wherein cross linking is carried out in the presence of a crosslinker selected from bisacrylamide, glutaraldehyde, adipic acid, dihydrazide, or combinations thereof at a concentration of 0.05 to 10% mass by mass basis of the total reaction mass.

9. The non-composite and composite superabsorbents as claimed in claim 1, wherein reaction of the backbone of the biopolymer, inorganic filler, monomer, initiator, and cross linker is achieved in a polar solvent selected from water, methanol, ethanol, propanol, or combinations thereof.

10. The superabsorbents as claimed in claim 1, for use in diverse fluid absorption and/or release situations such as in agriculture, medical, sanitary products, cosmetics and others, particularly the agricultural applications.

11. The non-composite and composite superabsorbents as claimed in claim 1, wherein the combination of biopolymers are prepared in a ratio of 50:50 of a first biopolymer to a second biopolymer.

12. The non-composite and composite superabsorbents as claimed in claim 1, wherein the combination of biopolymers and the at least one inorganic filler are prepared in a ratio of 90:10 to 10:90.

13. The non-composite and composite superabsorbents as claimed in claim 3, wherein the at least one inorganic filler comprises a clay or a combination of at least two clays, a clay and zeolite, or a clay and carbonaceous materials, wherein the carbonaceous materials are selected from ash derived from wheat, ash derived from rice husk, biochar derived from sugarcane molasses, or combinations thereof.

14. The non-composite and composite superabsorbents as claimed in claim 6, wherein the chemical initiator further comprises a co-initiator at a concentration of 0.01 to 5%, on mass by mass basis of total reaction mass.

15. The non-composite and composite superabsorbents as claimed in claim 9, wherein reaction of the backbone of the biopolymer, inorganic filler, monomer, initiator, and cross linker is achieved in pure water alone at 5 to 20 times the mass at a temperature of 40 to 80° C.

16. The non-composite and composite superabsorbents as claimed in claim 9, wherein reaction of the backbone of the biopolymer, inorganic filler, monomer, initiator, and cross linker is achieved through irradiation in a microwave oven for a period of 2 seconds to five minutes.

17. The non-composite and composite superabsorbents as claimed in claim 1, wherein the superabsorbents are xerogels.

18. The non-composite and composite superabsorbents as claimed in claim 17, wherein the xerogels possess a water absorption potential of at least 15,000 percent, on mass by mass basis of the mass of composite.

19. The non-composite and composite superabsorbents as claimed in claim 17, wherein the xerogels have a particle size of 1 mm to 100 nm.

* * * * *

UNITED STATES PATENT AND TRADEMARK OFFICE
CERTIFICATE OF CORRECTION

PATENT NO. : 9,833,767 B2  
APPLICATION NO. : 13/701342  
DATED : December 5, 2017  
INVENTOR(S) : Anupama Singh et al.

Page 1 of 1

It is certified that error appears in the above-identified patent and that said Letters Patent is hereby corrected as shown below:

On the Title Page

Item (75), Inventors Column 1, Line 2, delete "Druba" and insert -- Dhruba --

Signed and Sealed this  
Twenty-fourth Day of April, 2018

Andrei Iancu  
*Director of the United States Patent and Trademark Office*